United States Patent [19]

Erwin

[11] 4,125,771
[45] Nov. 14, 1978

[54] APPARATUS FOR DETERMINING STRESS IN NICKEL AND TITANIUM ALLOYED MATERIALS

[75] Inventor: Robert C. Erwin, Calabasas, Calif.

[73] Assignee: NET Systems Inc., Woodland Hills, Calif.

[21] Appl. No.: 852,799

[22] Filed: Nov. 18, 1977

[51] Int. Cl.² .................. G01N 23/20; G21K 1/00
[52] U.S. Cl. ............................ 250/277 R; 250/278
[58] Field of Search .................. 250/273, 272, 277 R, 250/278, 510

[56] References Cited

U.S. PATENT DOCUMENTS

| | | | |
|---|---|---|---|
| 3,402,291 | 9/1968 | Weinman | 250/277 |
| 3,639,758 | 2/1972 | Shimura | 250/278 |

Primary Examiner—Alfred E. Smith
Assistant Examiner—T. N. Grigsby
Attorney, Agent, or Firm—W. Edward Johansen

[57] ABSTRACT

The present invention is an improvement for use in combination with an apparatus for determining stress and percent retained austenite in a specimen so the apparatus may be used to analyze both Nickel and Titanium alloyed materials. The apparatus includes a first X-ray source with either a copper or cobalt target which irradiates with an X-ray beam a surface area of the specimen impinging on the surface area at a particular angle and a second X-ray source with either a copper or cobalt target which irradiates with an X-ray beam the same surface area of the specimen simultaneously impinging at another particular angle. The apparatus also includes a first detector tube and a second detector tube, each of which has a combination filter of iron oxide and steel foil, for detecting diffracted X-rays in particular crystallographic planes. The apparatus further includes circuitry which is independently responsive to the output of the first and second detector tubes for providing outputs proportional to the intensities of the diffracted X-rays, positioning mechanism for positioning the first and second detector tubes in response to the difference of the outputs and angular detecting mechanism for detecting angular position of the first and second detector tubes. The improvement includes the alignment of the first and second detector tubes so that the diffracted X-rays travel the same distance thereto from the specimen in order to maintain a circle of focus.

5 Claims, 6 Drawing Figures

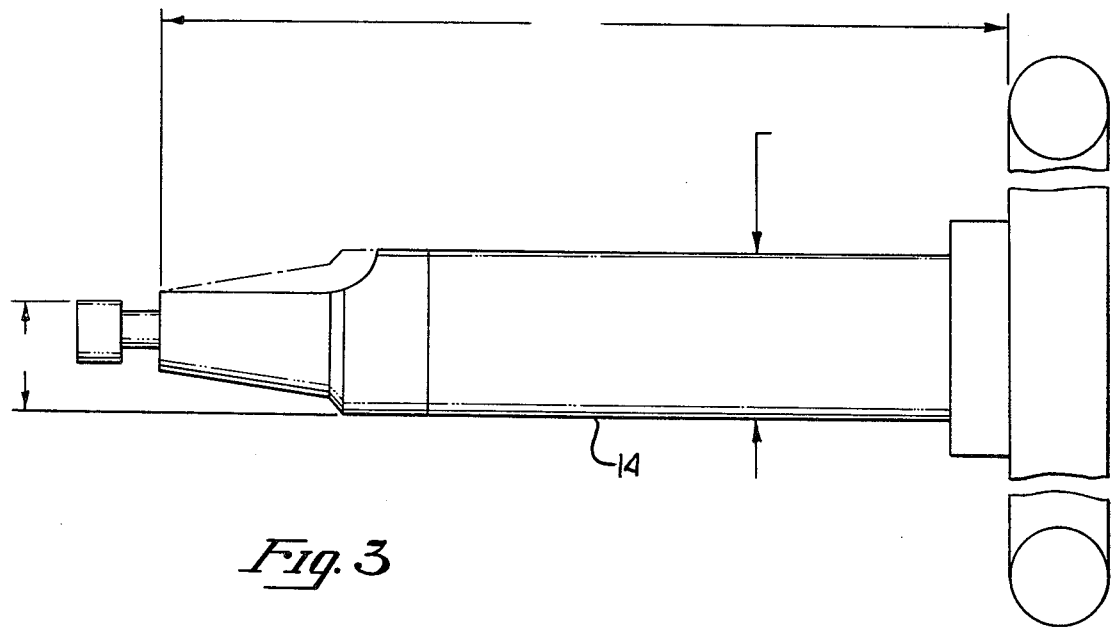
Fig. 3
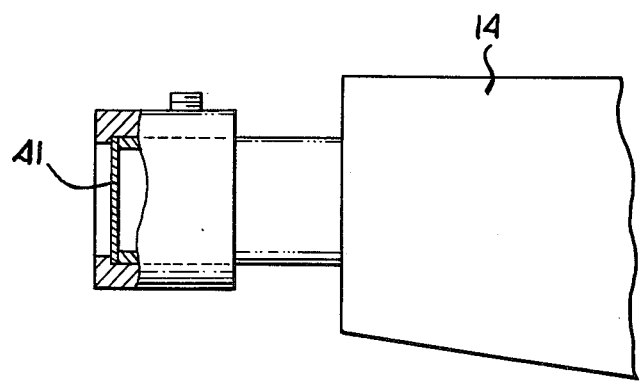
Fig. 4
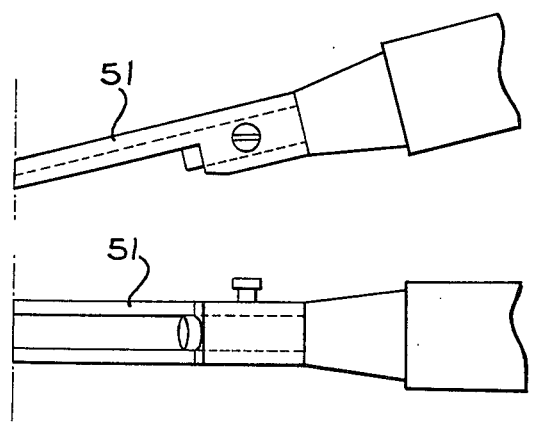
Fig. 5
Fig. 6

APPARATUS FOR DETERMINING STRESS IN NICKEL AND TITANIUM ALLOYED MATERIALS

BACKGROUND OF THE INVENTION

1. Field of the Invention

The invention relates to an apparatus and method for measuring residual stress in metals and other crystalline materials and the amount of second phase such as austenite in irons and steel by X-ray diffraction, and more particularly to an apparatus and method for measuring non-destructively the residual stress in Titanium and Nickel alloyed materials.

2. Description of the Prior Art

U.S. Pat. No. 3,402,291, entitled Method and Apparatus of Measuring Residual Stress and the Amount of a Known Constituent, issued to Eric W. Weinman on Sept. 17, 1968, teaches an invention which advances the measurement of residual stress and percent retained austenite from a slow laboratory procedure to automatic determination within seconds permitting continuous monitoring of residual stress and percent austenite in production parts. In accordance with this invention, two X-ray sources simultaneously radiate first and second X-ray beams at selected angles of incidence with a common specimen area. Individual detecting devices are provided for measuring background intensity and for automatically locating the true peak positions of the first X-ray beam as diffracted from martensite and austenite planes parallel to the specimen surface and the true peak position of the second X-ray beam as diffracted from equivalent martensite planes oblique to the specimen surface. A device indicates the residual stress as a function of the diffraction angle locations of the martensite diffraction peaks and another device indicates percent retained austenite as a function of the austeniste and martensite diffraction peaks as a function of the relative intensities thereof, which is the measured intensity less the background intensity.

The prior art apparatus includes a device that has two X-ray sources which are placed at different angles to simultaneously irradiate a common area of the sample. The device also has two sets of detector tubes. The output of each set drives a null-seeking mechanism that locates two points of equal corrected intensity for each peak. Corrections for angle-dependent factors are made electrically so that the output of the two detector tubes in a set are proportional to true intensities. At the null point, the true peak position lies midway between the two detector tubes. Poteniometers driven by the gear system at the end of each detector arm indicate the 0° and 45° peak position directly. The recorder is calibrated to read directly in psi because the difference between these voltages is proportional to stress.

The non-destructive X-ray analysis of stress in iron and steel has been very successful, but until presently no one has been able to measure residual stress in Titanium or Nickel alloyed materials using the device of U.S. Pat. No. 3,402,291. The inventor has determined that much redesign and modification of this device must be done in order to measure residual stress in a Titanium alloyed material.

SUMMARY OF THE INVENTION

In view of the foregoing factors and conditions characteristic of the prior art it is a primary object of the present invention to provide an apparatus for determining the stress in either a Nickel or a Titanium alloyed material.

It is another object to provide an apparatus for determining stress that can be modified by an extension member to not only maintain its circle of focus, but also enlarge its circle of focus.

It is still another object of the present invention to provide an apparatus for determining stress that in accordance with an embodiment of the present invention, an improvement for use in combination with an apparatus for determining stress and percent retained austenite in a specimen so the apparatus may be used to analyze both Nickel and Titanium alloyed materials is disclosed. The apparatus includes a first X-ray source with either a copper or cobalt target which irradiates with an X-ray beam a surface area of the specimen impinging on the surface area at a particular angle and a second X-ray source with either a copper or cobalt target which irradiates with an X-ray beam the same surface area of the specimen simultaneously impinging at another particular angle. The apparatus also includes a first detector tube and a second detector tube, each of which has a combination filter of iron oxide and steel foil, for detecting diffracted X-rays in particular crystallographic planes. The apparatus further includes circuitry which is independently responsive to the output of the first and second detector tubes for providing outputs proportional to the intensities of the diffracted X-rays, positioning mechanism for positioning the first and second detector tubes in response to the difference of the outputs and angular detecting mechanism for detecting angular position of the first and second detector tubes. The improvement includes the alignment of the first and second detector tubes so that the diffracted X-rays travel the same distance thereto from the specimen in order to maintain a circle of focus.

The features of the present invention which are believed to be novel are set forth with particularity in the appended claims.

Other objects and many of the attendant advantages of this invention will be more readily appreciated as the same become better understood by reference to the following detailed description and considered in connection with the accompanying drawing in which like reference symbols designate like parts throughout the figures.

DESCRIPTION OF THE DRAWING

FIG. 3 is a plan view of a detector tube of the apparatus of FIG. 1 which has been adjusted to increase the angle of diffraction.

FIG. 4 is a partial cross-sectional view of the tip of the detector tube of FIG. 3 showing a combination filter element.

FIG. 5 is a plan view of an extension member which is adapted to be mechanically coupled to the end of one of the X-ray sources of FIG. 1 to enlarge the circle of focus.

FIG. 6 is a side elevational view of the extension member of FIG. 5.

DESCRIPTION OF THE PREFERRED EMBODIMENT

Figure 1:
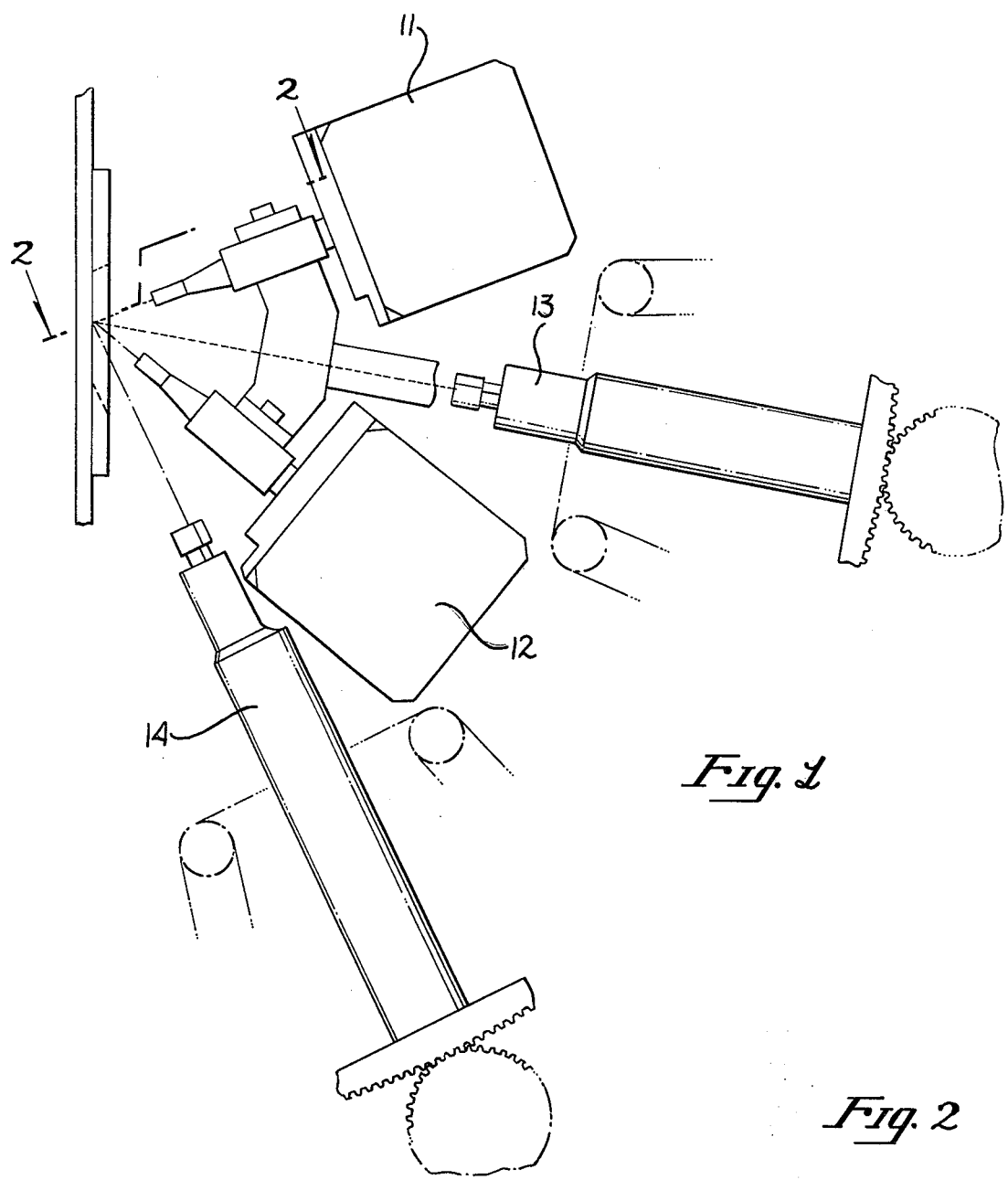
FIG. 1 is a schematic view of an appartus for determining stress in either a Nickel or a Titanium alloyed specimen in accordance with the principles of the present invention.

In order to best understand the present invention it is necessary to understand the operation of an apparatus for determining stress and percent retained austenite in a specimen by X-ray diffraction which is taught by U.S. Pat. No. 3,402,291. This apparatus is shown in FIG. 1 and it includes a first X-ray source 11 having a target of chrome and a second X-ray source 12 having a target of chrome, which irradiate with X-ray beams a surface area simultaneously impinging at two different angles, which are measured about the surface area and are approximately 45° apart. The distances that the X-ray beams of X-ray sources 11 and 12 travel are equal. It is necessary that these distances remain equal for the apparatus to operate. The apparatus also includes a first detector tube 13 and a second detector tube 14 for detecting diffracted X-rays in particular crystallographic planes which are equivalent.

The basic apparatus is taught in U.S. Pat. No. 3,402,291.

Figure 2:
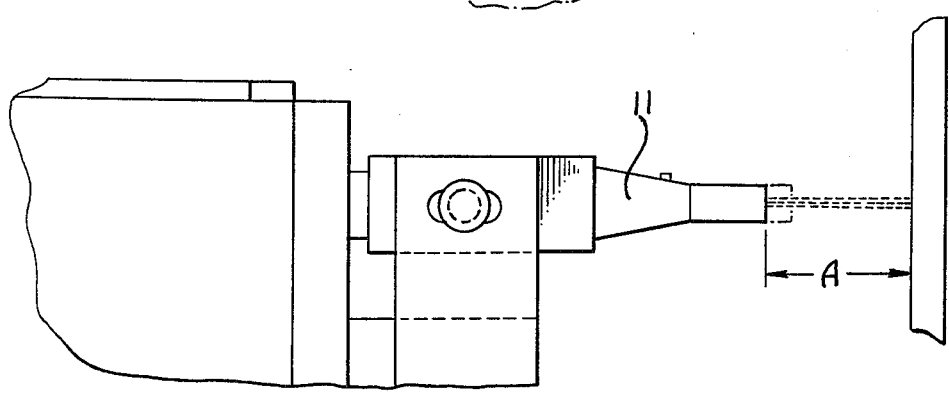
FIG. 2 is a partial side elevational side view of an X-ray source of the apparatus of FIG. 1 which has been adjusted to maintain the circle of focus.

Referring now to FIG. 2 the first X-ray source 11 is separated a particular distance, A, from the specimen, the change in which is approximately 0.450 inch. The second X-ray source 12 is moved about from the first X-ray source 11 by a distance of 0.175 inch perpendicularly to the parallel X-ray beam of the second X-ray source 12.

Both the first and second X-ray sources 11 and 12, when used for measuring stress in a titanium specimen, have targets formed from cobalt and, when used for measuring stress in nickel specimen, have targets formed from copper.

Referring again to FIG. 1 the second detector tube 14 is moved away from the specimen along the diffract X-ray beam a distance of 1.125 inch in order to equalize the detector to specimen distances for both the first detector tube 13 (4=0°) and the second detector tube 14 (4=45°). All of these physical changes to the apparatus taught in U.S. Pat. No. 3,402,291 are necessary to maintain the enlarged circle of focue required for the testing of titanium and nickel specimen.

Referring now to FIG. 3 the second detector tube 14 the detector has been redesigned to obtain full scale, 152° to 162°, of two-theta (2θ) diffraction angles. Referring now to FIG. 4 in conjunction with FIG. 3 each of the two detector tubes 13 and 14 a filter combination 41 that includes a 0.001 inch to 0.0020 inch steel foil filter element and a 0.001 inch to 0.006 inch oxide filter element in order to filter out the high amount of fluorescence, which is detrimental to the signal to noise ratio. The most optimum filter combination 41 is 0.0011 inch steel foil and 0.004 inch iron oxide.

Referring now to FIG. 5 in conjunction with FIG. 6, which are a plan view and a side elevational view, respectively, of a columnator foot 51 which provides a correct X-ray tube to specimen distance for the enlarged circle of focus. The columnator foot 51 is mechanically coupled to the tip of the first X-ray source 11.

The inventor has also found that an increase in power to 30 KVP and 15 M. A. was essential in order to minimize the effects of fluorescence by providing the strongest diffraction peaks obtained from a titanium specimen. The inventor in attempting to obtain a "0" stress reference with the use of titanium powder discovered that the diffraction peak was too sharp to be located automatically as with steel and aluminum. The inventor also discovered that in order to establish the proper two-theta (2θ) angle range a diffraction peak would be needed prior to evaluation. The diffraction peak would be taken from the titanium specimen in question. The inventor has determined that the stress factor to calibrate the equipment for the titanium specimen in question is approximately 45,000 psi.

From the foregoing it can be seen that an apparatus for measuring stress in both nickel and titanium specimens has been described. It should be noted that the figures and schematic are not drawn to scale, and distances of and between the figures are not to be considered significant.

Accordingly, it is intended that the foregoing disclosure and showing made in the drawing shall be considered only as illustrations of the principles of the invention. The invention is set forth with particularity in the appended claims.

What is claimed is:

1. An improvement for use in combination with an apparatus for determining stress and percent retained austenite in a specimen containing both austenite and martensite crystalline structure by X-ray diffraction which includes:
   a. a first X-ray source having a target of a particular material which irradiates with an X-ray beam a surface area of the specimen impinging on the surface area at a particular angle;
   b. a second X-ray source having a target of a particular material which irradiates with an X-ray beam the same surface area of the specimen simultaneously impinging at another particular angle;
   c. a first detecting tube for detecting diffracted X-rays from a particular crystallographic plane;
   d. a second detector tube for detecting diffracted X-rays from another equivalent and particular crystallographic plane;
   e. first and second circuit means which are independently response to the outputs of the first and second detector tubes for providing outputs proportional to the intensities of the diffracted X-rays;
   f. positioning means for positioning the first and second detector tubes in response to the difference of the outputs of the first and second circuit means; and
   g. detecting means for detecting the angular position of the first and second detector tubes, said improvement comprising:
      a. a filter element of steel foil in the range of 0.0001 inches to 0.0021 inches; and
      b. a second filter of iron oxide in the range of 0.001 inches to 0.010 inches in combination with said first filter element, said combination optically coupled in the path of each detector tube; and
      c. means for maintaining a circle of focus for the first and second detector tubes and for the first and second x-ray tubes.

2. An improvement according to claim 1 for use in combination with apparatus for determining stress in specimen of Titanium alloyed material wherein the appropriate material for forming the target is copper and wherein said means for retaining a circle of focus comprises:
   a. means for equalizing the distance traveled by the X-ray beam of the first X-ray source and the distance traveled by X-ray beam of the second X-ray source; and b. means for equalizing the distance traveled by the diffracted X-rays to the first detector tube and the distance traveled by the diffracted X-rays to the second X-rays.

3. An improvement according to claim 2 for use in combination with apparatus for determining stress in a specimen of Titanium alloyed material wherein said mean for maintaining a circle of focus also comprises:
   a. an extension member which is mechanically coupled to the end of the first x-ray source so that the specimen of Titanium alloyed material is disposed a particular distance from the first and second X-ray sources.

4. An improvement according to claim 1 for use in combination with apparatus for determining stress in a specimen of Nickel alloyed material wherein the appropriate material for forming the target is cobalt and wherein said means for retaining a circle of focus comprises:
   a. means for equalizing the distance traveled by the X-ray beam of the first X-ray source and the distance traveled by X-ray beam of the second X-ray source; and
   b. means for equalizing the distance traveled by the diffracted X-rays to the first detector tube and the distance traveled by the diffracted X-rays to the second X-rays.

5. An improvement according to claim 2 for use in combination with apparatus for determining stress in a specimen of Nickel alloyed material wherein said means for maintaining a circle of focus also comprises:
   a. an extension member which is mechanically coupled to the end of the first X-ray source so that the specimen of Nickel alloyed material is disposed a particular distance from the first and second X-ray sources.

* * * * *

UNITED STATES PATENT AND TRADEMARK OFFICE
CERTIFICATE OF CORRECTION

PATENT NO. : 4,125,771

DATED : November 14, 1978

INVENTOR(S) : Robert C. Erwin

It is certified that error appears in the above-identified patent and that said Letters Patent are hereby corrected as shown below:

On the title page, item [73] Assignee, should be deleted in its entirety.

Signed and Sealed this

Sixth Day of November 1979

[SEAL]

Attest:

RUTH C. MASON
Attesting Officer

LUTRELLE F. PARKER
Acting Commissioner of Patents and Trademarks